United States Patent
Vogler et al.

(10) Patent No.: US 9,562,759 B2
(45) Date of Patent: Feb. 7, 2017

(54) OPTICAL COHERENCE TOMOGRAPHY TECHNIQUE

(75) Inventors: Klaus Vogler, Eckental/Eschenau (DE); Henning Wisweh, Moehrendorf (DE)

(73) Assignee: Wavelight GmbH (DE)

( * ) Notice: Subject to any disclaimer, the term of this patent is extended or adjusted under 35 U.S.C. 154(b) by 78 days.

(21) Appl. No.: 14/345,369

(22) PCT Filed: Sep. 26, 2011

(86) PCT No.: PCT/EP2011/004813
§ 371 (c)(1),
(2), (4) Date: Mar. 20, 2014

(87) PCT Pub. No.: WO2013/044932
PCT Pub. Date: Apr. 4, 2013

(65) Prior Publication Data
US 2015/0002850 A1    Jan. 1, 2015

(51) Int. Cl.
*G01B 9/02* (2006.01)
*A61B 3/10* (2006.01)

(52) U.S. Cl.
CPC .......... *G01B 9/02091* (2013.01); *A61B 3/102* (2013.01); *G01B 9/02004* (2013.01);
(Continued)

(58) Field of Classification Search
CPC ............ G01B 9/02091; G01B 9/02069; G01B 9/02004; G01B 9/02014; G01B 2290/20; A61B 3/102
See application file for complete search history.

(56) References Cited

U.S. PATENT DOCUMENTS

| | | | |
|---|---|---|---|
| 7,292,345 B2 * | 11/2007 | Hadley et al. | 356/479 |
| 2002/0172456 A1 * | 11/2002 | Hosomi et al. | 385/27 |

(Continued)

FOREIGN PATENT DOCUMENTS

| | | |
|---|---|---|
| JP | 2002-333536 A2 | 5/2001 |
| JP | 2008-264137 A2 | 11/2008 |

(Continued)

OTHER PUBLICATIONS

Moon et al.; "Ultra-high-speed optical coherence tomography with a stretched pulse supercontinuum source"; Optics Express, OSA (Optical Society of America); Nov. 27, 2006; pp. 11575-11584; vol. 14; No. 24; ISSN: 1094-4087.

(Continued)

*Primary Examiner* — Kara E Geisel
*Assistant Examiner* — Dominic J Bologna

(57) ABSTRACT

An optical coherence tomography device comprises a light generator, a dispersive medium, an optical coupler and a detector. The light generator is adapted to generate a series of input pulses of coherent light, each input pulse having an input pulse width. The dispersive medium has an input that is optically coupled to the light generator and an output for output pulses. The dispersive medium is adapted to stretch the input pulse width to an output pulse width of each of the output pulses by chromatic dispersion. The optical coupler is adapted to couple the output pulses into a reference arm and a sample arm. The optical coupler is further adapted to superimpose light returning from the reference arm and the sample arm. The detector is adapted to detect an intensity of interference of the superimposed light with a temporal resolution of a fraction of the output pulse width.

21 Claims, 6 Drawing Sheets

(52) U.S. Cl.
CPC ..... *G01B 9/02014* (2013.01); *G01B 9/02069* (2013.01); *G01B 2290/20* (2013.01)

(56) References Cited

U.S. PATENT DOCUMENTS

| | | | |
|---|---|---|---|
| 2003/0086647 A1* | 5/2003 | Willner et al. | 385/37 |
| 2006/0051016 A1* | 3/2006 | Ogawa | B82Y 20/00 385/27 |
| 2007/0024856 A1* | 2/2007 | Izatt | A61B 3/102 356/456 |

FOREIGN PATENT DOCUMENTS

| | | |
|---|---|---|
| JP | 2009-015156 A2 | 1/2009 |
| JP | 2009-150649 A2 | 7/2009 |
| JP | 2009-222531 A2 | 10/2009 |
| JP | 2009-273550 | 11/2009 |

OTHER PUBLICATIONS

Tae-Jung et al.; "Ultrarapid Optical Frequency-Domain Reflectometry Based Upon Dispersion-Induced Time Stretching: Principle and Applications"; IEEE Journal of Selected Topics in Quantum Electronics, IEEE Service Center; vol. 18; No. 1; Mar. 21, 2011; pp. 148-165; ISSN: 1077-260X.

* cited by examiner

Spectral-Temporal Power Distribution $S_{IN}$

200a

Spectral-Temporal Power Distribution $S_{OUT}$

300a

Spectral-Temporal Power Distribution $S_{IN}$

Spectral-Temporal Power Distribution $S_{OUT}$

OPTICAL COHERENCE TOMOGRAPHY TECHNIQUE

CROSS REFERENCE TO RELATED APPLICATIONS

This application is a section 371 national stage phase of International Application No. PCT/EP2011/004813, filed 26 Sep. 2011, titled "OPTICAL COHERENCE TOMOGRAPHY TECHNIQUE," which is hereby incorporated by reference in its entirety.

TECHNICAL FIELD

The present disclosure relates to a technique for Optical Coherence Tomography (OCT). More specifically, and not by way of limitation, the disclosure relates to a device for OCT including a pulse-stretched swept light source and to a method of performing OCT using a pulse-stretched broadband light source.

BACKGROUND

Optical Coherence Tomography (OCT) is a non-invasive, and often non-contact, imaging technique. Light with a defined coherence length is radiated on a sample that reflects or re-emits light at different depths of penetration, which encodes information in the phase of the light. The light from the sample is superimposed with coherent light of a reference branch.

Classical OCT systems used a movable mirror in a mechanical reference branch for a variable optical length of the reference branch. Modern OCT systems use Fourier Domain OCT (FD-OCT). The performance of an OCT system may be characterized by its axial resolution and/or its axial scanning depth.

In some of the existing OCT systems, the axial resolution or the axial scanning depth may be limited by features of the OCT system. By way of example, an OCT system using Spectral Domain OCT (SD-OCT, which is one case of FD-OCT) may have an axial scanning depth limited by the spectral resolution of a spectrometer. As another example, an OCT system using Swept Source OCT (SS-OCT, which is another case of FD-OCT) may have an axial scanning depth limited mainly by the instantaneous linewidth $\delta\lambda$ of the swept source. Further, an OCT system using FD-OCT may have an axial resolution that cannot be adjusted independently of its axial scanning depth. For example, the scanning depth $\Delta z_{max}$ may be proportional to the axial resolution $\delta z_{min}$ for a given spectral or temporal resolution of the detector. Moreover, an SS-OCT system may have a lower axial resolution, because its swept source of light is tunable over an overall spectral bandwidth $\Delta\lambda$ (also referred to as tuning range) that is narrower than a complete bandwidth $\Delta\lambda$ of a light source usable for SD-OCT without tuning of the light source.

SUMMARY

There is a need for an optical coherence tomography technique that improves, under at least certain conditions, limitations of an axial resolution and/or of a scanning depth.

According to one aspect, a device for optical coherence tomography, or OCT, according to claim 1 is provided. The device comprises a light generator adapted to generate a series of input pulses of coherent light, each input pulse of the series having an input pulse width; a dispersive medium having an input optically coupled to the light generator and an output for output pulses, wherein the dispersive medium is adapted to stretch the input pulse width to an output pulse width of each of the output pulses by means of chromatic dispersion; an optical coupler adapted to couple the output pulses from the output into a reference arm and into a sample arm, and to superimpose light returning from the reference arm and from the sample arm; and a detector adapted to detect an intensity of interference of the superimposed light with a temporal resolution of a fraction of the output pulse width.

Each input pulse of the series may have a full bandwidth $\Delta\lambda$, also referred to as input spectral range. The optical coupler may be a beam splitter, e.g., a fiber-based beam splitter or a free-space beam splitter. The fraction of the output pulse width can be denoted by $\delta t_{gate}$.

The term "light", as used herein, may include electromagnetic waves having (vacuum) wavelengths in the range of 600 nm to 1500 nm, preferably in the range of 650 nm to 1050 nm, or in the range of 850 nm to 1250 nm, or in the range of 1100 nm to 1500 nm.

Some embodiments may allow changing an axial resolution of the OCT by changing a parameter related to the light generator (e.g., a bandwidth of the light generator, also referred to as input spectral range). The same or some other embodiments may allow changing an axial scanning depth of the OCT by changing a parameter related to the dispersive medium (e.g., one or more dispersion parameters of the dispersive medium, a length and direction of a path of light propagation in the dispersive medium) and/or a parameter related to the detector (e.g., a duration of the fraction). Further, the axial resolution and the axial scanning depth may be independently changeable in some of the embodiments. A spectrometer and/or widely tunable light generator (e.g., tunable in the full bandwidth $\Delta\lambda$) simultaneously capable of producing a very narrow instantaneous bandwidth (which may also be denoted by the symbol $\delta\lambda$) may be omittable in certain embodiments.

Each input pulse in the series or the entire series may have an input spectral range that is at least essentially time-independent. Alternatively or in addition, each input pulse in the series or the entire series may have an input center wavelength that is at least essentially time-independent. Each output pulse may have a time-averaged output spectral range that at least essentially corresponds to the input spectral range.

Each output pulse may have an instantaneous output peak wavelength (also denoted by the symbol $\lambda(t)$). The instantaneous output peak wavelength may be time-dependent and/or different for different fractions of the output pulse width. The instantaneous output peak wavelength may change monotonically with time (over a period corresponding to the output pulse width). Alternatively or in addition, each output pulse may have an instantaneous output spectral range (also denoted by the symbol $\delta\lambda$). The instantaneous output spectral range is also referred to as an instantaneous bandwidth, an instantaneous linewidth or an instantaneous output spectral interval. The instantaneous output spectral range may be time-dependent and/or different for different fractions of the output pulse width. The instantaneous output spectral range may shift monotonically with time (over a period corresponding to the output pulse width). The input spectral range may be multiple times broader than one or each of the instantaneous output spectral ranges.

The dispersive medium may include an optical fiber or a waveguide. The waveguide may include grating structures, e.g. Dispersive Bragg Gratings (DBG). The optical fiber may include grating structures, e.g. chirped Fiber Bragg Gratings (chirped FBG). A path of light propagation in the dispersive medium may be essentially straight. Alternatively or in addition, the path of light propagation may be folded. The folded path may include reflections at an interface or a boundary of the medium. The path of light propagation in the dispersive medium from the input to the output may be at least 1 km and/or up to 10 km, up to 60 km or up to 100 km (e.g., in fiber). Furthermore, the path may have a length of at least 1 cm or 2 cm and/or up to 20 cm or 50 cm (e.g., in a waveguide or a Bragg crystal).

The input pulse may spectrally spread along the path of propagation. The spectral spread may give rise to a correlation of wavelength and output time. The instantaneous output peak wavelength of the output pulse may be correlated to an output time. The output time may be defined relative to an input pulse generation time of the light generator. The output time may be linear in the wavelength $\lambda$ or linear in a wavenumber, $$k = \frac{2\pi}{\lambda}.$$

The dispersive medium may include a plurality of taps at different positions along the path of light propagation. The device may further comprise an optical switch adapted to selectively couple the light generator to one of the taps as the input. Alternatively or in addition, the optical switch may be adapted to selectively couple one of the taps as the output to the optical coupler.

The chromatic dispersion of the dispersive medium may be a linear dispersion. I.e., the dispersion parameter may be essentially independent of the wavelength in the input spectral range or linear in the wavenumber, $k=2\pi/\lambda$. The dispersion may be a group-velocity dispersion. A dispersion, parameter of the dispersive medium may be equal to or greater than 10000 ps/(km·nm), preferably approximately 13200 ps/(km·nm) or greater. The dispersion parameter may be proportional to a second derivative of an index of refraction of the medium with respect to wavelength. The dispersion may be positive. The positive dispersion may correspond to a negative dispersion parameter. Long wavelengths in the output pulse may be temporally ahead of short wavelengths in the output pulse. The dispersive medium may output long wavelengths first in each output pulse. The peak instantaneous wavelength of each output pulse may sweep from long wavelengths to short wavelengths (i.e., positively "chirped"). The input pulse may be un-chirped. The output pulse may be up-chirped (in case of positive dispersion). Alternatively, the output pulse may be down-chirped (in case of negative dispersion).

The device may further comprise a field generator adapted to generate an external field. The external field may act on the dispersive medium. The dispersion parameter of the medium may be controlled or controllable by a strength of external field.

The dispersive medium may be distinct from a gain medium of the light generator. The dispersive medium may be outside of a gain medium of the light generator.

The detector may detect the intensity of at least one of the time-dependent instantaneous output peak wavelength ($\lambda(t)$) and the time-dependent instantaneous output spectral range ($\lambda(t)-\delta\lambda/2 \ldots \lambda(t)+\delta\lambda/2$). The detector may further be adapted to sample the intensity for a plurality of consecutive fractions. Each of the intensities detected for the respective fractions need not be spectrally resolved. The plurality of sampled fractions may essentially cover the output pulse width or a period corresponding to the output pulse width.

The dispersive medium may be configured to provide the output pulse. The output pulse may have an instantaneous output peak wavenumber, k(t), changing as a function of time. The instantaneous output peak wavenumber k(t) may change linearly in time. The output pulse may have a "chirp" that is non-linear in the wavelength $\lambda(t)$ and/or linear in k(t) (also referred to as a "linear-in-k chirp"). A chirp that is linear in the wavenumber may be provided by a Photonic-Crystal Fiber (PCF). The detector may be adapted to sample the fractions uniformly in time, e.g., at equal intervals or periodically. Alternatively, the dispersive medium may be configured to provide a "chirp" that is not linear in the wavenumber, k(t). The chirp may be linear in the wavelength, $\lambda(t)$, or frequency, $\omega(t)$. The detector may be adapted to sample the fractions linearly in the wavenumber k. The detector may be calibrated to a linear change of the wavenumber k(t) (i.e., an essentially linear function of time) or to a non-linear change of the wavenumber k(t) (as a non-linear function of time). The detector may be calibrated by means of an optical clocking, e.g. a k-clocking. The optical clocking may include a Mach-Zehnder interferometer. The optical clocking may follow or track the change in the wavenumber in real-time. Alternatively or in addition, the detector may include a storage in which a calibration table may be encoded. The calibration table may relate wavenumber and time. The calibration table may include or represent a tabulated function k(t). The calibration table may be determined and/or encoded at a time of manufacturing the device or prior to performing the OCT. Any other method of calibration may also be applied. The detector may sample the intensity of interference of the fractions at times defined by the calibration table. Sampling the intensity of interference of the fractions in a manner that is linear in the wavenumber may avoid a loss in the signal of the interference (also referred to as a modulation signal), particularly may avoid a fall-off in sensitivity and/or signal-to-noise ratio (SNR). Further, requirements for a processing unit may be reduced, since no intermediate processing step of generating data linear in the wavenumber may be required.

The fraction, or each of the fractions, may be equal to or shorter than 1/500, 1/1000 or 1/10000 of the output pulse width, or may have a duration between 1/10000 and 1/500 of the output pulse width. The plurality of sampled fractions (per output pulse) may be at least 500, or at least 1000, or at least 10000. Alternatively or in addition, the fraction, or each of the fractions, may be shorter than 200 ns, preferably shorter than 100 ns.

The detector may include a photodiode or a dual balanced detector unit. The dual balanced detector unit may allow reducing relative intensity noise of the light generator. The detector may further include a gate unit (which is also referred to as gate electronics) connected to the photodiode. The gate unit may be adapted to chop an intensity signal according to the fraction and/or read the intensity for each of the sampled fractions. The detector may include a buffer adapted to store the intensity readings of the plurality of sampled fractions. The detector may include a processor adapted to Fourier transform the intensity readings (which correspond to one output pulse) and/or other signal processing functions.

The light generator may be a wideband light generator. The light generator may be adapted to generate the input pulses over a wideband spectrum. The light generator may include a titanium-sapphire laser (also referred to as Ti-sapphire laser or TIS laser) or any other short-pulse laser or ultra-short pulse laser. The center wavelength may be in the range of 750 nm to 850 nm, preferably approximately 800 nm. The input spectral range may be approximately equal to or greater than 200 nm (e.g. 300 nm or 400 nm). The titanium-sapphire laser may be pulsed. Alternatively or in addition, the light generator may include a Super Luminescent Diode (SLD) or any other broadband light source, e.g. an Amplified Spontaneous Emission Source (ASE source) or a pulsed supercontinuum light source. The supercontinuum light source may include at least one of picosecond laser, a nanosecond laser and a non-linear fiber coupled to the laser. The non-linear fiber may be configured to generate a broad and essentially continuous spectrum by means of non-linear optical effects.

The detector and the light generator may be synchronized. A controller connected to the light generator and the detector may be adapted for synchronous control. The synchronization may include a fixed time shift. The time shift may be a time delay between the generation of the input pulses and the sampling of the intensities of the plurality of fractions. The series of input pulses may be periodic. The light generator may generate the series of input pulses at a repetition rate. The sampling may be initiated or triggered at the same repetition rate. The repetition rate may define an A-line acquisition rate of the OCT.

The light generator may include a continuous wave light source (CW light source) and an optical shutter. The shutter may be operatively arranged between the CW light source and the input of the dispersive medium. The shutter may be adapted to periodically chop or block light from the CW light source. The shutter may operate at a shutter frequency corresponding to the repetition rate. The shutter frequency may be at least 10 kHz, 20 kHz or 50 kHz. The shutter frequency may be up to 100 kHz, 500 kHz, 1 MHz or 3 MHz.

The optical coupler may include at least one of a beam splitter and an optical fiber coupler. The optical coupler may couple the output into the arms with equal intensity. Alternatively, the optical coupler may couple the output into the arms with different intensities so as to increase the intensity of the sample arm. The sample arm may provide back-scattered light. The back-scattered light may be scattered from a sample. The beam splitter may include a partially transparent mirror, e.g. a semi-transparent mirror. The optical coupler may be an optical fiber coupler. The optical fiber coupler may be a fused-fiber coupler or include a fiber tapering. The optical coupler may be a 2-by-2 coupler. The optical coupler may be a 50%-50% division coupler or may deliver any other spitting ratio. Alternatively or in addition, the optical coupler may include a circulator. The circulator may be a three-port circulator. A first port of the circulator may be coupled to the output. A second port of the circulator (in the direction of circulation) may be coupled to a 1-by-2 coupler. A third port of the circulator (in the direction of circulation) may be coupled to the detector.

According to another aspect, a method of performing optical coherence tomography, or OCT, according to claim 19 is provided. The method comprises generating a series of input pulses of coherent light, each input pulse of the series having an input pulse width; stretching the input pulse width of each of the input pulses to an output pulse width of output pulses by means of chromatic dispersion in a dispersive medium; coupling the output pulses from the output into a reference arm and into a sample arm, and superimposing light returning from the reference arm and from the sample arm; and detecting an intensity of interference of the superimposed light with a temporal resolution of a fraction of the output pulse width.

The method may be performed by the device. The method may further comprise any feature or step mentioned in the context of the device aspect.

BRIEF DESCRIPTION OF THE DRAWINGS

Further features, advantages and technical effects of the disclosure will become apparent in below detailed description of exemplary embodiments with reference to the accompanying drawings, in which.

DETAILED DESCRIPTION

Figure 1:
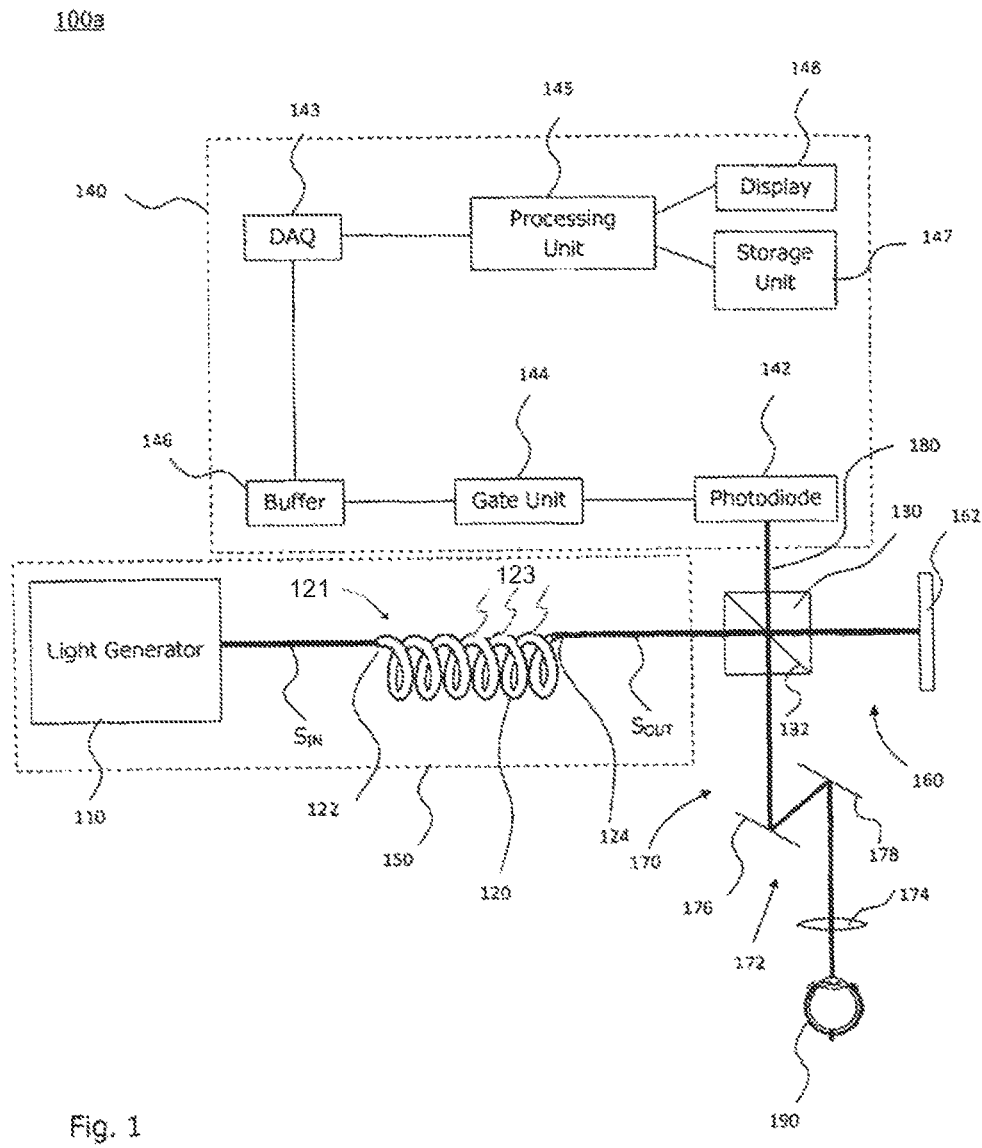
FIG. 1 schematically illustrates a first embodiment of a device for optical coherence tomography including a dispersive medium.

Modern Optical Coherence Tomography (OCT) is dominated by so-called Fourier Domain OCT (FD-OCT), which achieves a better Signal-to-Noise Ratio (SNR) compared to classical Time Domain OCT (TD-OCT). Furthermore, by avoiding a mechanical z-scan (i.e., a reference arm which optical length is mechanically changed), significantly higher scanning rates, e.g., $f_R$>100 kHz, are realizable. The FD-OCT is implemented as Spectral Domain OCT (SD-OCT) or Swept Source OCT (SS-OCT).

A modern SD-OCT system is described in the article "Extended in vivo interior eye-segment imaging with full-range complex spectral domain optical coherence tomography" by J. Jungwirth et al. in the Journal of Biomedical Optics, page set 050501, Vol. 14 (5), 2009. An intrinsic limitation of a scanning depth and a way of doubling the limited scanning depth by means of a so-called full-range complex (FRC) technique is discussed.

An SS-OCT system is described with reference to FIG. 2 in the article "High-speed optical frequency-domain imaging" by S. H. Yun et al. in Optics Express, Vol. 11, No. 22, pages 2953-2963. Aside the scanning rate, a bandwidth $\Delta\lambda$ emitted by a light source of an OCT device and a instantaneous linewidth $\delta\lambda$ of the emission bandwidth $\Delta\lambda$ significantly influence a performance of the OCT device, including an axial resolution $\delta z_{min}$ and an axial scanning depth $\Delta z_{max}$, as detailed below.

The axial resolution $\delta z_{min}$ (in both SD-OCT and SS-OCT) is determined by the bandwidth $\Delta\lambda$ of the light source according to:

$$\delta z_{min} = \frac{2\ln 2}{\pi} \frac{\lambda_0^2}{n\Delta\lambda},$$

wherein n denotes an index of refraction of a sample, such as tissue. For example, n=1.37 for a cornea of an eye. The symbol $\lambda_0$ denotes a center wavelength in the bandwidth $\Delta\lambda$ defined by the Full Width at Half Maximum (FWHM) bandwidth of the light source.

A limitation of the axial scanning depth $\Delta z_{max}$ is set, in SD-OCT and SS-OCT, by the spectral resolution $\delta\lambda$ of detection or the instantaneous linewidth of the swept laser, respectively, according to:

$$\Delta z_{max} = \frac{\ln 2}{n\pi} \frac{\lambda_0^2}{\delta\lambda},$$

wherein $\lambda_0$ and n denote the center wavelength and the index of refraction, respectively. In the case of SD-OCT using a spectrometer with a linear detector array, the spectral resolution $\delta\lambda$ is limited by a pixel size of the linear detector array, on which a transversely decomposed spectrum of light is radiated.

Physical principles underlying FD-OCT thus relate limits of the scanning depth $\Delta z_{max}$ and the axial resolution $\delta z_{min}$ according to:

$$\Delta z_{max} = \frac{\Delta\lambda}{2 \cdot \delta\lambda} \delta z_{min}.$$

Consequently, a requirement for an SD-OCT system may aim at detecting the full spectral width (i.e., aiming at a large $\Delta\lambda$) and, at the same time, may aim at a high spectral resolution (i.e., at a small $\delta\lambda$). However, the spectral resolution $\delta\lambda$ and the bandwidth $\Delta\lambda$ covered by the detector are not independent but related by a number of pixels in the linear detector array. If the spectral resolution $\delta\lambda$ is improved by increasing the transversal spread of the spectral decomposition that is radiated on the linear detector array, the bandwidth $\Delta\lambda$ covered by the linear detector array may be reduced. Manufacturable pixel size and the number of pixels in the linear detector array of spectrometers, as well as apertures of achromatic lenses and diffraction gratings, determine technical limitations to independently improving the axial resolution $\delta z_{min}$ and the scanning depth $\Delta z_{max}$.

The technical limitations thus limit the performance of SD-OCT systems and may exclude certain applications. By way of example, modern SD-OCT systems may achieve a rather high axial resolution $\Delta z_{min}$, but with a relatively low scanning depth $\Delta z_{max}$, as illustrated by below numerical example.

Using a Ti-sapphire laser (TiS laser) as the light source with central wavelength $\lambda_0$=800 nm and a rather advanced bandwidth $\Delta\lambda$=200 nm in conjunction with an advanced pixel number of N=4096 pixels, a good axial resolution $\delta z_{min}$=1.0 μm and a scanning depth $\Delta z_{max}$=2.1 mm in tissue with n=1.37 is possible. In this example, the limited number of pixels entails a limited spectral resolution $\delta\lambda = \Delta\lambda/N = 200$ nm/4096 px=0.05 nm/px, which in turn limits the scanning depth $\Delta z_{max}$. The high axial resolution thus obviates a large scanning depth, and vice versa.

In the case of SS-OCT, a laser light source is rapidly tuned through the entire emittable bandwidth $\Delta\lambda$, resulting in an instantaneous linewidth $\delta\lambda$ with which the laser light source oscillates at a time t of the tuning. The instantaneous bandwidth $\delta\lambda$ is, however, limited by a quality factor (or Q factor) of a cavity of the laser light source and by a settling time of the oscillation. Moreover, the bandwidth $\Delta\lambda$ of tunable light sources required for SS-OCT is typically below 120 nm, which is why SS-OCT often achieves lower axial resolutions $\delta z_{min}$ at a slightly wider scanning depth $\Delta z_{max}$ compared to SD-OCT. Furthermore, currently no laser light sources for SS-OCT with sufficient tunable bandwidth $\Delta\lambda$ are available in a spectral range covering $\lambda_0$=800 nm, which significantly reduces the axial resolution, since $\delta z_{min}$ is proportional to the square of $\lambda_0$. Using very advanced swept laser light sources, a SS-OCT system may achieve the performance of below numerical example.

Assuming the swept laser light sources has a center wavelength $\lambda_0$=1060 nm, a total bandwidth $\Delta\lambda$=120 nm and provides an instantaneous line width $\delta\lambda$=0.06 nm, results in an axial resolution $\delta z_{min}$=3.0 μm (for cornea tissue) or $\delta z_{min}$=4.1 μm (in air) and a scanning depth $\Delta z_{max}$=3.0 mm (for cornea tissue) or $\Delta z_{max}$=4.1 mm (in air).

As has become apparent from above principle considerations for FD-OCT and corresponding numerical examples, a high axial resolution $\delta z_{min}$ and a wide scanning depth $\Delta z_{max}$ cannot be simultaneously realized.

FIG. 1 schematically illustrates an arrangement of optical components and their mutual coupling according to a first embodiment of a device 100a for optical coherence tomography. The device 100a comprises a light generator 110, a dispersive medium 120 having an input 122 and an output 124, an optical coupler 130, and a detector 140. The light generator 110 is optically coupled to the input 122. The light generator 110 and the dispersive medium 120 form a light source 150 of the device 100a.

The optical coupler 130 receives the light that is output by the light source 150 and equally splits the light by means of a semi-transparent mirror 132 into a reference arm 160 terminated by a mirror 162 and into a sample arm 170. Light propagating towards the coupler 130 in the reference arm 160 and in the sample arm 170 is superimposed by the coupler 130 in a detection arm 180.

The detector 140 comprises a photodiode 142, a gate unit 144, a buffer 146, a data acquisition unit 143, a processing unit 145, a storage unit 147 and a display 148. The photodiode 142 is arranged on the detection arm 180. The photodiode 142 has a response time below 50 ps, preferably on the order of 35 ps or 40 ps, or therebetween. A temporal resolution may also depend on dead time of the photodiode of approximately 100 ps, which can be reduced or avoided by consecutively using more than one photodiode 142 or more than one detector 140. The gate unit 144 is electrically connected to the photodiode 142. The gate unit 144 sequences an intensity signal of the photodiode 142 in temporal fractions $\delta t_{gate}$. The buffer 146 temporarily stores samples of the sequenced intensity signal. Each sample represents one fraction in the sequence of fractions. The buffer 146 stores the intensity of each fraction in association with a consecutive number of the fraction, a detection time, or a time-dependent wavelength (which is detailed with reference to FIGS. 5 and 7). The data acquisition unit 143 is an interface via which the processing unit 145 retrieves the data of those fractions corresponding to one of the output pulses 302, 304, 306.

The processing unit is adapted to read the intensity samples of one sequence from the buffer 146 via the data acquisition unit 143 and to perform a Fourier transformation thereof. A result of the Fourier transform is permanently stored in the storage unit 147 and/or displayed to a user at the display 148.

The sample arm 170 comprises an xy-scanner 172 and a scanner lens 174. The xy-scanner 172 includes a pair of pivotable mirrors 176 and 178 that deflect the light in the sample arm 170 (propagating either from the coupler 130 to the lens 174 or in the other direction) in a first transversal direction and a second transversal direction perpendicular to the first transversal direction, respectively. The scanning lens 174 forms an approximately Gaussian beam spot, which beam waist is focused inside a sample 190, such as the cornea or retina of an eye.

Figure 2:
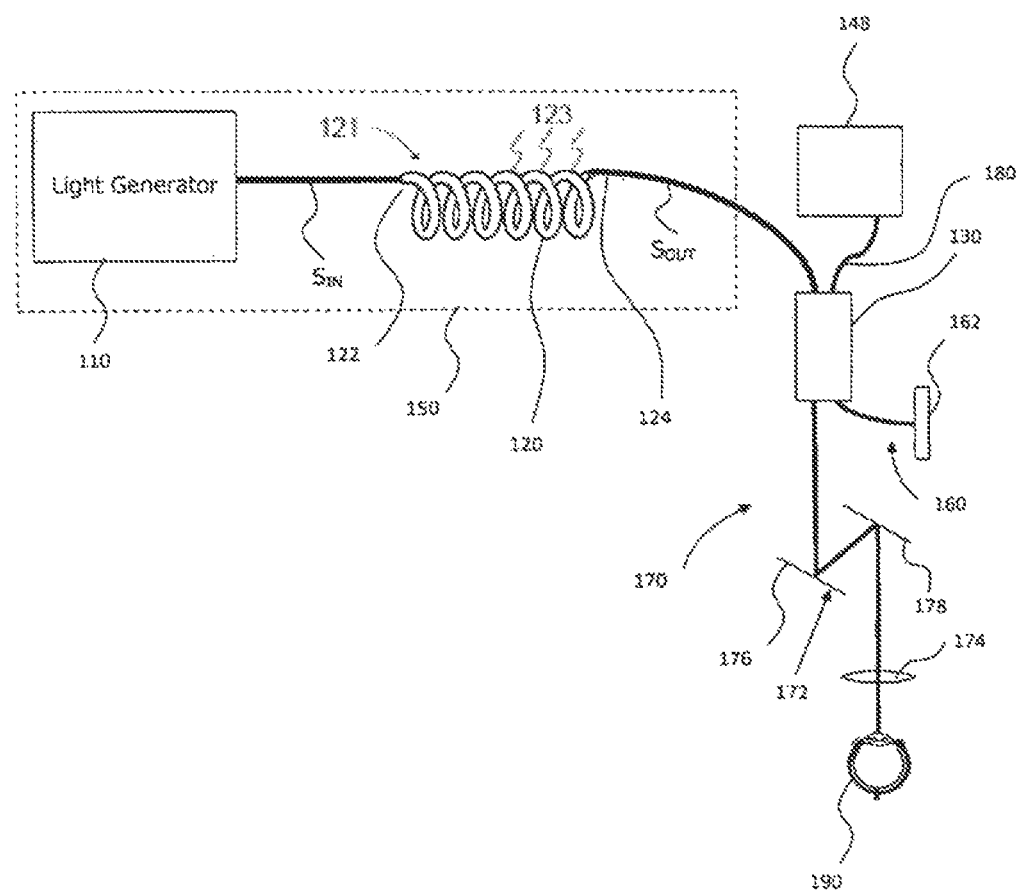
FIG. 2 schematically illustrates a second embodiment of a device for optical coherence tomography including a dispersive medium.

FIG. 2 schematically illustrates a second embodiment of a device 100b for optical coherence tomography. Corresponding reference signs relate to components and features as described in the context of the embodiment 100a. The device 100b differs in that the optical coupler 130 includes a 2-by-2 fused-fiber coupler. A first interface pair of fused fibers is optically coupled to the output 124 of the dispersive medium 120 and to the detector 148, respectively. A second interface pair of the fused fibers is optically coupled to the xy-scanner 172 and the reference arm 160, respectively.

Figure 3:
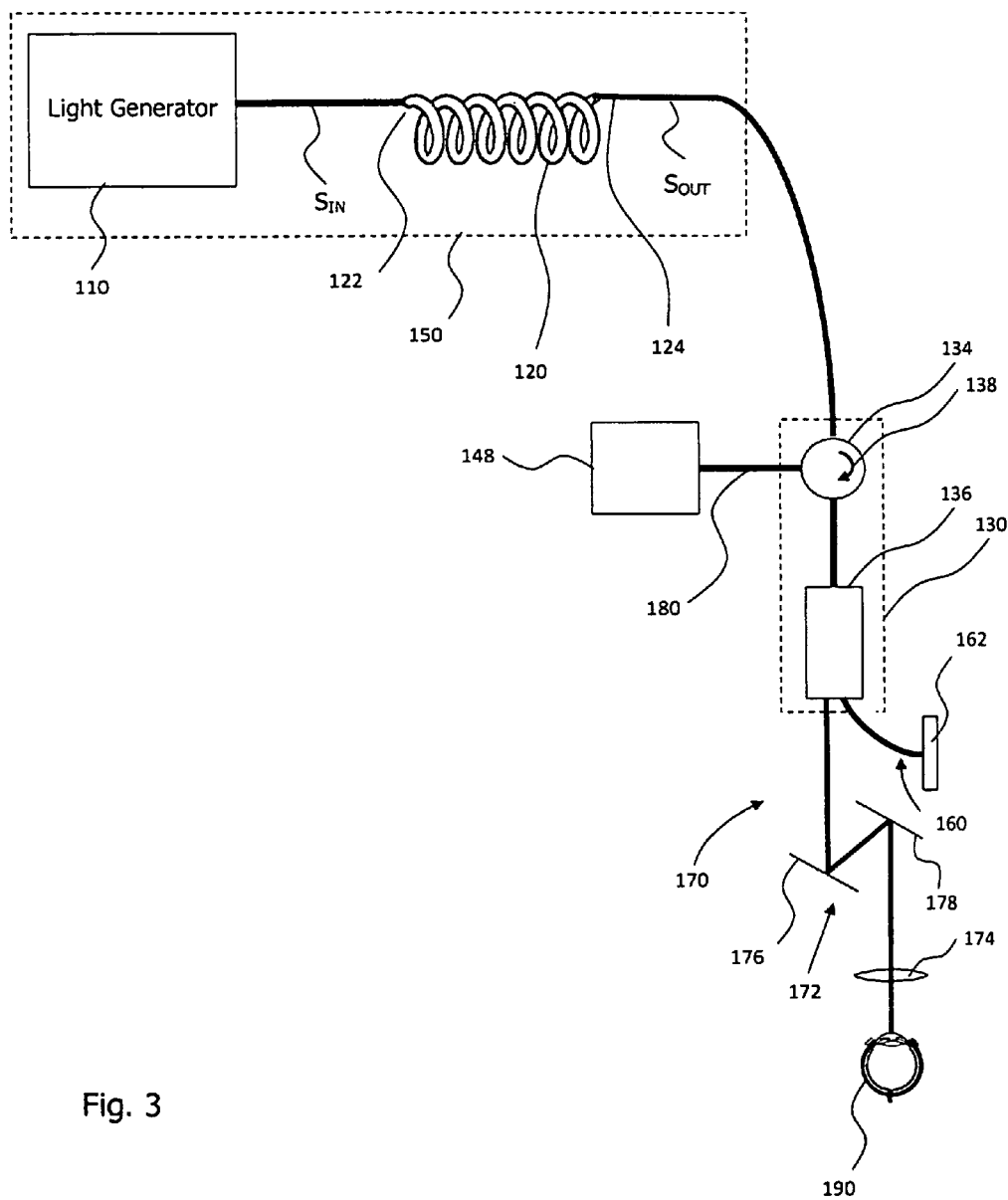
FIG. 3 schematically illustrates a third embodiment of a device for optical coherence tomography including a dispersive medium.

FIG. 3 schematically illustrates a third embodiment of a device 100c for optical coherence tomography. The device 100c includes components and features denoted by corresponding reference signs as described above with reference to the FIG. 1 or 2. The device 100c differs in that the optical coupler 130 includes a circulator 134 and a 1-by-2 coupler 136. The circulator 134 has three ports and is adapted to transmit power entering any port to a next port in a circulation direction indicated by an arrow 138. A first port of the circulator 134 is optically coupled to the output 124 of the dispersive medium 120. A second port (that follows the first port in the direction of circulation) of the circulator 134 is optically coupled to the single port of the 1-by-2 coupler 136. A third port (that follows the second port in the direction of circulation) of the circulator 134 defines the detection arm 180. The 1-by-2 coupler 136 outputs light from the second port of the circulator 134 into both the reference arm 160 and the sample arm 170. Light returning from the reference arm 160 and/or the sample arm 170 is combined into the single port of the 1-by-2 coupler and thus enters the second port of the circulator 134. One or both of the reference arm 160 and the sample arm 170 optionally includes a polarization controller.

Figure 4:
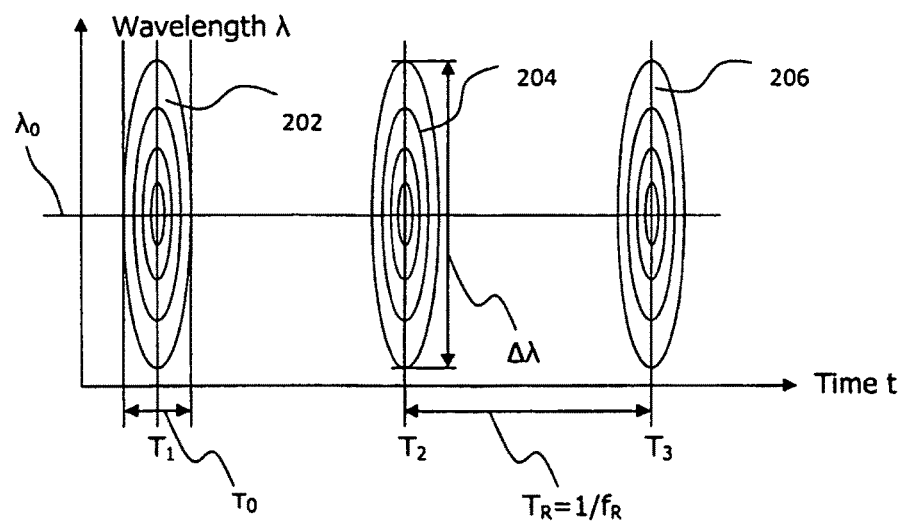
FIG. 4 shows a schematic diagram of a first input power distribution at an input of the dispersive medium of FIG. 1, 2 or 3.
Figure 6:
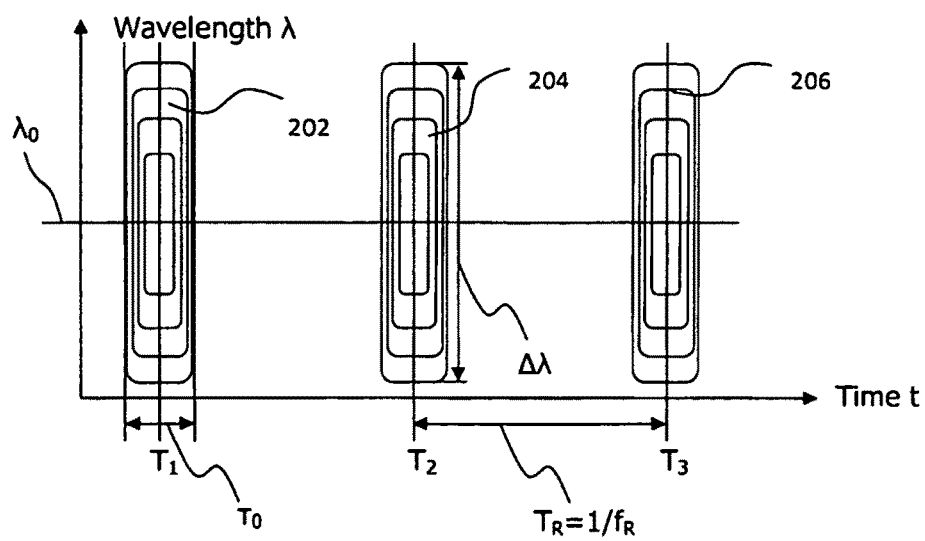
FIG. 6 shows a schematic diagram of a second input power distribution at an output of the dispersive medium of FIG. 1, 2 or 3.

The light generator 110 is a broadband TiS laser or a pulsed supercontinuum source (SC source). The light generator 110 generates pulses with a center wavelength $\lambda_0$=800 nm, 1050 nm or 1300 nm at a repetition rate $f_R=1/T_R$ of the pulses. A spectral-temporal power distribution $S_{IN}$ for (a short portion of) a series of pulses 202, 204 and 206 at times $T_1$, $T_2$, and $T_3$ is schematically illustrated in a diagram 200a of FIG. 4. Time is shown on the horizontal axis and wavelength on the vertical axis of the diagram 200a. The spectral-temporal power distribution is schematically illustrated as a spectral-temporal density that is a function of both time and wavelength. FIG. 6 schematically illustrates in a diagram 200b a variant of the spectral-temporal power distribution $S_{IN}$ at the input 122. Extreme wavelengths in the wide spectral range $\Delta\lambda$ are provided by the light generator 110 over essentially the full pulse width $\tau_0$. Closed lines schematically indicate lines of equal power density.

In a variant of each of the devices 100a, 100b and 100c, the light generator 110 includes a broadband Continuous Wave (CW) light source, such as a super luminescent diode (SLD) or an Amplified Spontaneous Emission (ASE). The CW light source has a high intensity or luminescence. The CW light source provides a broadband spectrum corresponding to the input spectral range $\Delta\lambda$. The CW light source is optically chopped by means of a fast shutter. The shutter operates at a frequency of approximately $f_R$=1 MHz. The chopped light is input to the dispersive medium 120. The diagram 200b in FIG. 6 may schematically illustrate (e.g., more realistically than the diagram 200a in FIG. 4) the spectral-temporal power distribution $S_{IN}$ provided by the shutter.

Each pulse 202, 204 or 206 in the series of pulses is essentially identical as to its distribution of power in time and frequency or wavelength. The TIS laser pulses have an input spectral range $\Delta\lambda$ on the order of 200 nm. An exemplary TIS laser is described in the article "Compact, low-cost Ti:Al$_2$O$_3$ laser for in vivo ultra high-resolution optical coherence tomography" by A. Unterhuber et al., Optics Letters, Vol. 28, No. 11, p. 905-907, 2003. An input pulse width $\tau_0$ is a pulse duration defined as the time of power above a $1/e^2$-level with respect to a power peak. (An alternative definition uses a −3 dB level, i.e. the FWHM in time.) The input pulse width $\tau_0$ is in the range of 10 fs to 10 ns, preferably 1 ps to 1 ns or 2 ns. The input spectral range $\Delta\lambda$ is defined as the FWHM bandwidth, i.e. at a −3 dB level of the spectrum. An alternative definition may use a level of −10 dB (i.e. the spectral range is defined at a 10%-level) for complex spectra, or rarely at a $1/e^2$-level. The input spectral range $\Delta\lambda$ defines an effective swept spectrum by means of the dispersive medium 120, as described below with reference to FIGS. 5 and 7.

The broadband input pulse 202, 204 or 206 is stretched in time as the pulse passes through the highly dispersive medium 120. In the embodiments 100a, 100b and 100c shown in the FIGS. 1, 2 and 3, respectively, the dispersive medium 120 is an optical fiber. The input pulse is subject to a linear dispersion of group velocity. The alternative of a non-linear group velocity dispersion is discussed below with reference to FIG. 8. As a result, spectral components of the input pulse are differently delayed or temporally dispersed with respect to each other. The delay is a function of the wavelength such that, in the case of positive dispersion, long wavelengths propagate faster in the dispersive medium 120 resulting in output pulses 302, 304, and 306, which spectral-temporal power distribution $S_{OUT}$ is schematically illustrated by diagram 300a in FIG. 5. A spectral-temporal power distribution $S_{OUT}$ at the output 124 of the dispersive medium 120 resulting from the input pulses according to the diagram 200b of FIG. 6 is schematically illustrated by diagram 300b in FIG. 7. An original spectrum 308 of the input pulses 202, 204 and 206 is essentially unchanged when averaged over a time scale longer than an output pulse with $\tau_p$ of each of the output pulses 302, 304 and 306. More specifically, non-linear effects such as a parametric gain, a second-harmonic generation, a dispersion of arbitrary orders, a self-phase modulation and a four-wave mixing are absent or negligible in the dispersive medium 120. The dispersive medium 120 is a linear medium. Specifically, the center wavelength $\lambda_0$ is conserved.

Figure 5:
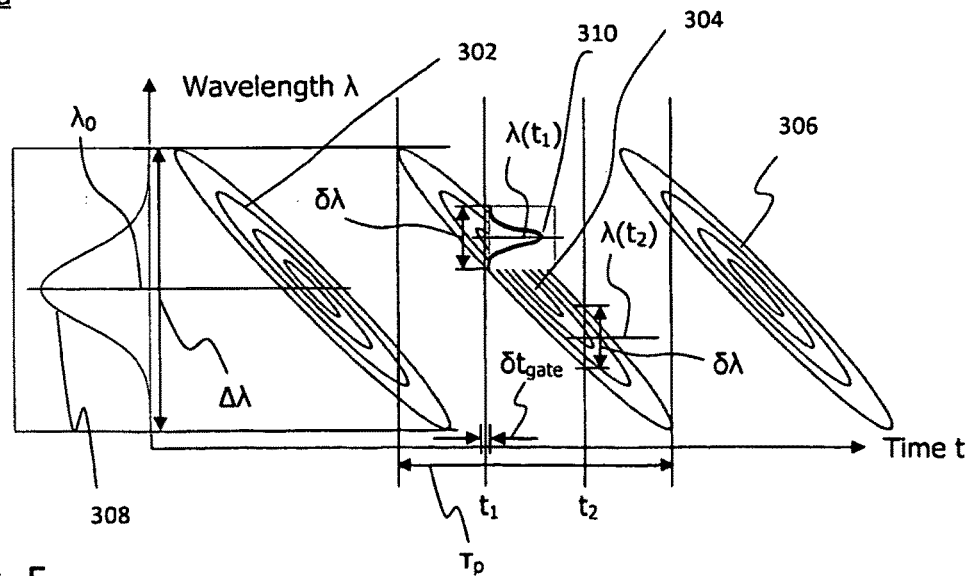
FIG. 5 shows a schematic diagram of a first output power distribution at an output of the dispersive medium of FIG. 1, 2 or 3 as a result of the first input power distribution.
Figure 7:
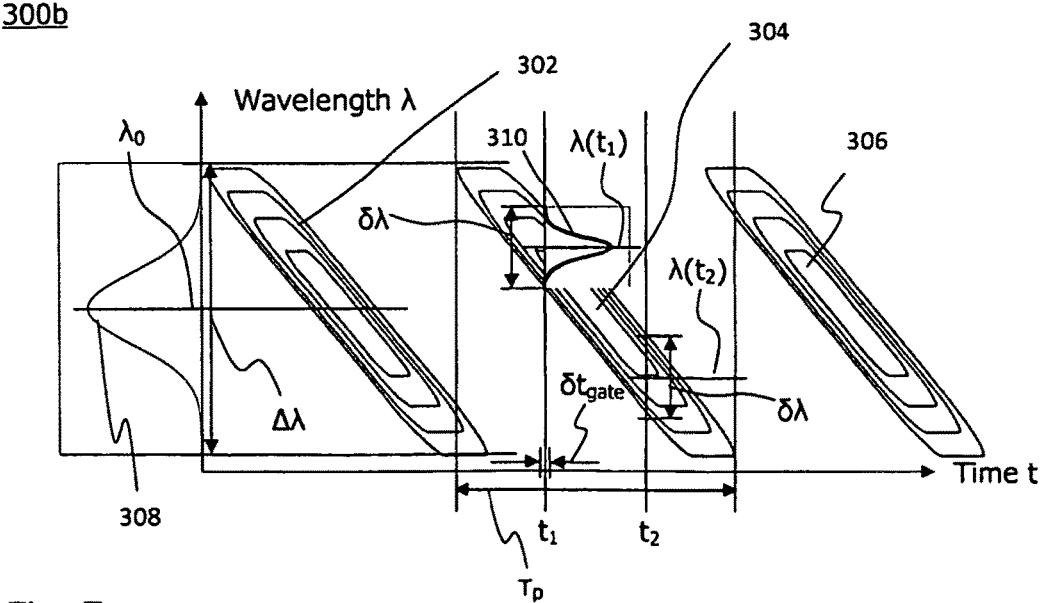
FIG. 7 shows a schematic diagram of a second output power distribution at an output of the dispersive medium of FIG. 1, 2 or 3 as a result of the second input power distribution.

On the significantly shorter time scale of the fractions $\Delta t_{gate}$ temporarily resolved by detector 140, the spectral separation of different wavelengths gives rise to an "up-chirped" output pulse, which wavelength λ(t) is a function of time, as is indicated in each of the diagrams 300a and 300b for the times $t_1$ and $t_2$. An instantaneous output spectrum 310, exemplarily shown for the instant $t_1$ in FIGS. 5 and 7, is a narrow line with an instantaneous spectral range δλ out of the full input spectral range Δλ.

The dispersion of the medium 120 is a chromatic dispersion or a group-velocity dispersion (GVD). The dispersion is (at least partially) described by a dispersion parameter D. Specifically designed fibers are available with large dispersion parameters for almost any given spectral range Δλ of interest, particularly for 600 nm to 1000 nm. Large Mode Area fibers (LMA fibers) are Photonic Chrystal Fibers (PCF) provide a GVD of the different spectral components with the dispersion parameter |D|>500 ps/(nm·km).

Figure 8:
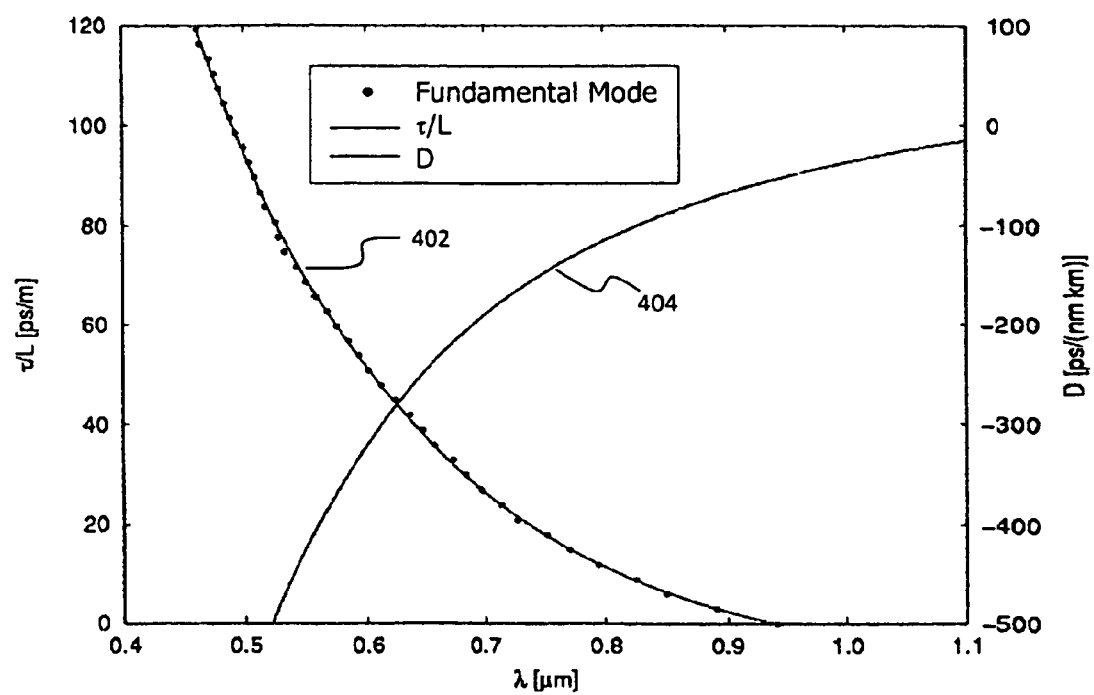
FIG. 8 shows a measurement diagram of a dispersion parameter of the dispersive medium of FIG. 1, 2 or 3.

FIG. 8 shows a diagram 400 of the dispersion for a polarization maintaining Large Mode Area UV fiber. The diagram 400 is a measurement result of Prof. P. Hartmann, Westsächsische Hochschule. The LMA UV fiber has a diameter of 125 µm, a first Mode Field Diameter MFDx=2.6 µm and a second Mode Field Diameter MFDy=4.3 µm. A delay per length, τ/L, is shown with reference sign 402 and the dispersion parameter D is shown with reference sign 404. Corresponding results on the dispersion parameter of a PCF are provided in the journal Optics Express, Vol. 12, No. 2, 2004 on p. 301 in FIG. 1(a). Furthermore, an advanced variant of the each of embodiments of the devices 100a, 100b and 100c uses a so-called "concentric-core fiber" with a dispersion parameter D on the order of −13200 ps/(nm·km), as reported in the journal Laser Focus World, July 2011, p. 9.

The input pulse width $\tau_0$ of the input pulse 202, 204 or 206 is strongly stretched, i.e. prolonged in time, to the output pulse width $\tau_p$ of the output pulse 302. The input pulse width $\tau_0$ is on the order of 1 fs to 1 ns. The output pulse width $\tau_p$ is on the order of 100 ns to 10 µs. The dispersion of the medium 120 relates the output pulse width $\tau_p$ to the input pulse with $\tau_0$ according to:

$$\tau_p = \tau_0 + |D| \cdot L \cdot \Delta\lambda,$$

with the spectral dispersion parameter D of the dispersive medium 120 (in ps/(nm·km)), a length L of a path of light propagation (in km, e.g. the fiber length), and the input spectral range Δλ (in nm). Preferred lengths L include 1 km, 10 km or any length L in between, as detailed in below numerical example. A power of the light generator 110 is chosen such that the (peak) power of the output pulses 302, 304, 306 (e.g., at the output 124) is at least 1 mW, 5 mW, 10 mW, 20 mW, 50 mW or a power between 5 to 50 mW. The power may take into account an attenuation in the dispersive medium 120.

The broadband input spectrum $S_{IN}$ of the input pulses 202, 204 and 206 with the broad input spectral range Δλ and the short input pulse width $\tau_0$ is thus largely stretched in time to the output pulse with $\tau_p$ without changing the time-average spectral range Δλ at the output 124. In the case of positive dispersion shown in each of the FIGS. 5 and 7, red spectral components are in the beginning of the stretched output pulse 302, 304 or 306. Blue spectral components follow in a temporal tail of the output pulse 302, 304 or 306. The different spectral components thus reach the detector 140 at different times, which sequentially detects the spectral components in the fractions $\delta t_{gate}$ subdividing the output pulse width $\tau_p$.

The temporal spread, i.e., the output pulse width τp, is selected, depending on an application, by changing the dispersion parameter D. The dispersion parameter D is changed by selectively switching to the dispersive medium 120 out of a plurality of different dispersive media. In order to avoid moving components in the optical arrangement of the device 100a, 100b or 100c, a variant of the embodiment changes the dispersion parameter D by applying an external electric or magnetic field acting on a dispersive medium 120, wherein the dispersion parameter D of the medium 120 is sensitive to the external field. Alternatively or in addition, the length L of the dispersive medium 120 is changed. In an advanced variant of the embodiment of the device 100a, 100b or 100c, the dispersive medium 120 includes a plurality of taps 123 along the length L. Each of the plurality of taps allows coupling light into or out of the dispersive medium 120 at a position of the tap along the length L. At least one of the input 122 and the output 124 can be selected along the length L of the dispersive medium 120. An optical switch 121 automatically uses one of the taps 123 as the input 122 or as the output 124 depending on the application.

At a sufficient temporal dilatation of the output pulse 302, 304 or 306 (i.e., by a is sufficiently large $T_p$) and for a sufficiently fast detector 140 (i.e., for a sufficiently short $\delta t_{gate}$), only the sharp instantaneous spectral range δλ (i.e., the instantaneous spectral linewidth) is detected within the temporal fraction $\delta t_{gate}$ defined by the gate unit 144. The instantaneous output spectral range δλ (i.e., the instantaneous spectral linewidth) thus defines the coherence length, which is twice the axial resolution according to:

$$l_c = 2 \cdot \Delta z_{max} = \frac{2 \cdot \ln 2}{n \cdot \pi} \cdot \frac{\lambda_0^2}{\delta\lambda}.$$

Here it is assumed that the depth at which the OCT signal drops to −6 dB (corresponding to 20·log(A), wherein A is the amplitude of the signal) defines the axial resolution. In other words, the axial resolution $\Delta z_{max}$ is half of the coherence length. It is pointed out that, even for a given temporal resolution $\delta t_{gate}$ of the detector 140, the spectral resolution (i.e., the instantaneous spectral range δλ) can be improved by increasing the output pulse width $\tau_p$, which is caused by the dispersive medium 120, independently of the spectral range Δλ of the light generator 110 and/or to decrease the gate time resolution $\delta t_{gate}$.

As a result of the independence, the axial resolution $\delta z_{min}$ (which is proportional to 1/Δλ) and the axial scanning depth $\Delta z_{max}$ (which is proportional to 1/δλ, and thus proportional to $\tau_p/(\Delta\lambda \cdot \delta t_{gate})$) can be chosen independent of each other. In other words, the OCT technique, which may also be referred to as a Pulse-Stretched Swept Source OCT (PSSS-OCT), allows to almost freely choose the axial resolution $\delta z_{min}$ and the axial scanning depth $\Delta z_{max}$, e.g., depending on the application. The spectral resolution δλ is no longer limited by a pixel size of a detector array in a spectrometer (as opposed to SD-OCT) and is no longer determined by an instantaneous bandwidth of a tunable or swept light source (as opposed to SS-OCT). A large bandwidth Δλ (which is provided by the light source 110) and a small spectral resolution δλ (which is caused by the dispersive medium 120) are not mutually exclusive using the PSSS-OCT.

Parameters for an exemplary implementation of each of the devices 100a, 100b and 100c are summarized. The TiS laser used as the light generator has a center wavelength $\lambda_0$=800 nm and a bandwidth Δλ=200 nm for an input pulse width $\tau_0$=1 ps to 1 ns. The dispersive medium 120 is a fiber of L=2 km length arranged as a coil. The fiber has a dispersion parameter D=−13200 ps/(nm·km). The detector 140 has a temporal resolution for sampling the fractions $\delta t_{gate} \leq 100$ ps, which clocking is supported by all components 142 to 148 of the detector 140. The output pulse width $\tau_p$ is thus (at least, since the contribution of the first term, $\tau_0$, is neglected):

$$\tau_p = |D| \cdot L \cdot \Delta\lambda = 5.3 \text{ μs}.$$

For a sampling interval $\delta t_{gate} = 100$ ps, a plurality of N fractions is sampled per pulse:

$$N = \frac{5.3 \text{ μs}}{100 \text{ ps}} = 5.3 \cdot 10^4.$$

The instantaneous output spectral range $\delta\lambda$, which is the spectral resolution detected by the detector 140 detecting the intensity signal of the photodiode 142 in the temporal fraction $\delta t_{gate}$, is thus:

$$\delta\lambda = \frac{\Delta\lambda}{N} = 0.004 \text{ nm}.$$

The exemplary implementation of the device 100a, 100b or 100c can thus achieve an axial resolution $\delta z_{min} = 1.0$ μm and an axial scanning depth $\Delta z_{max} = 26$ mm. The embodiments of the devices 100a, 100b and 100c thus achieves the high axial resolution (comparable to SD-OCT) in combination with an axial scanning depth that (for sufficient signal strength, i.e., spectral power) is long enough to scan the entire length of an eye.

The scanning depth $\Delta z_{max}$ is freely adjustable, even without changing the optical arrangement of the device 100a, 100b or 100c, by changing the sampling interval of the fractions $\delta t_{gate}$.

Alternatively or in addition, particularly suitable for the case of a very short input pulse width $\tau_0$, the temporal spread of the input pulse yielding the output pulse of output pulse width $\tau_p$ may be described by the relation:

$$\tau_p = \tau_0 \sqrt{1 + \left(4 \cdot \ln(2) \cdot \frac{D_2}{\tau_0^2}\right)^2} \approx 4 \cdot \ln(2) \cdot \frac{D_2}{\tau_0},$$

wherein $D_2 = \beta_2 \cdot L$ is the Group Delay Dispersion (e.g., the Group Velocity Dispersion related to the specific length L of the dispersive medium). The symbol $\beta_2$ denotes the Group Velocity Dispersion:

$$\beta_2 = -\frac{D_\lambda \cdot \lambda_0^2}{2\pi \cdot c} \text{ (in units of } fs^2/m),$$

wherein $D_\lambda$ denotes the dispersion parameter (also referred to as Group Delay Dispersion Parameter) in units of ps/(km·nm), an example of which is shown in FIG. 8.

In a set of numerical examples, the dispersion parameter is $D_\lambda = -13200$ ps/(km·nm) and light is generated at a center wavelength $\lambda_0 = 800$ nm, which yields $\beta_2 = 4481781$ fs$^2$/m, such that for a length L=2 km the output pulse $\tau_p$ is approximately 1.65 μs; for a length L=10 km the output pulse $\tau_p$ is approximately 8.25 μs; or for a length L=20 km the output pulse $\tau_p$ is approximately 16.5 μs.

By further increasing the input spectral range $\Delta\lambda$ of the light generated by the TiS laser 110, the axial resolution $\delta z_{min}$ is further improved, even without a negative effect on the scanning depth $\Delta z_{max}$.

As has become apparent from above description of embodiments of a device for optical coherence tomography, some embodiments allow overcoming limitations or mutual interdependencies of at least one of the axial resolution $\delta z_{min}$ and a scanning depth $\Delta z_{max}$. An output pulse width $\tau_p$ can exceed 1 μs. The detector can resolve temporal fractions $\delta t_{gate}$ shorter than 100 ps. A dispersion can be linear with respect to a wavenumber or frequency of spectral components in an input pulse, which allows sampling the fractions $\delta t_{gate}$ of an intensity signal uniformly in time for direct Fourier transformation.

It will be apparent that various changes may be made in the form, construction and arrangement of above exemplary embodiments without departing from the scope of the invention or without sacrificing all of its advantages. Because the invention can be varied in many ways, it will be recognized that the invention should be limited only by the scope of the following claims.

The invention claimed is:

1. A device for optical coherence tomography, or OCT, the device comprising:
   a light generator adapted to:
      generate a series of input pulses of coherent light, each input pulse of the series having an input pulse; width and an input spectral range; and
      change an axial resolution of the device independently of an axial scanning depth of the device by changing the input spectral range;
   a single dispersive medium having an input optically coupled to the light generator and an output for output pulses, the dispersive medium being adapted to stretch the input pulse width to an output pulse width of each of the output pulses by chromatic dispersion, the dispersive medium comprising a plurality of taps at different positions along the length of the dispersive medium to provide different dispersion;
   an optical coupler adapted to couple the output pulses from the output into a reference arm and into a sample arm, and to superimpose light returning from the reference arm and from the sample arm;
   an optical switch adapted to change the axial scanning depth independently of the axial resolution by selectively coupling the light generator to one of the taps as the input or by selectively coupling one of the taps as the output to the optical coupler; and
   a detector adapted to detect an intensity of interference of the superimposed light with a temporal resolution of a fraction of the output pulse width.

2. The device of claim 1, wherein each input pulse in the series has an at least essentially time-independent input center wavelength.

3. The device of claim 1, wherein each output pulse has at least one of a time-dependent instantaneous output peak wavelength and a time-dependent instantaneous output spectral range.

4. The device of claim 3, wherein the input spectral range is multiple times broader than the instantaneous output spectral range.

5. The device of claim 1, wherein the dispersive medium includes an optical fiber.

6. The device of claim 1, wherein a path of light propagation in the dispersive medium from the input to the output is longer than 1 km.

7. The device of claim 1, wherein a dispersion parameter of the dispersive medium is greater than 10000 ps/(km·nm).

8. The device of claim 7, further comprising a field generator adapted to generate an external field acting on the medium, wherein the dispersion parameter of the medium is controlled or controllable by the external field.

9. The device of claim 1, wherein the detector is further adapted to sample the intensity for a plurality of consecutive fractions corresponding to one output pulse width.

10. The device of claim 9, wherein the plurality of sampled fractions is at least 500.

11. The device of claim 1, wherein the fraction is shorter than 200 ns.

12. The device of claim 1, wherein the detector includes at least one of a photodiode and a balanced detector.

13. The device of claim 12, wherein the detector further includes a gate unit connected to the photodiode and adapted to read the intensity for each of the fractions.

14. The device of claim 1, wherein the light generator includes a pulsed titanium-sapphire laser or a pulsed supercontinuum light source.

15. The device of claim 9, wherein the light generator generates the series of input pulses at a repetition rate and the detector initiates the sampling at the repetition rate.

16. The device of claim 1, wherein the light generator includes a continuous wave light source and a shutter operatively arranged between the continuous wave light source and the input of the dispersive medium.

17. The device of claim 1, wherein the optical coupler includes at least one of a beam splitter, an optical fiber coupler, a circulator and a 1-by-2-coupler.

18. A method of performing optical coherence tomography, or OCT, the method comprising:

generating by a light generator a series of input pulses of coherent light, each input pulse of the series having an input pulse width and an input spectral range;

stretching the input pulse width of each of the input pulses to an output pulse width of output pulses by means of chromatic dispersion in a single dispersive medium, the dispersive medium comprising a plurality of taps at different positions along the length of the dispersive medium to provide different dispersion;

changing an axial resolution for the OCT independently of an axial scanning depth for the OCT by changing the input spectral range;

changing the axial scanning depth independently of the axial resolution by selectively coupling the light generator to one of the taps as input or by selectively coupling one of the taps as output to an optical coupler;

coupling by the optical coupler the output pulses into a reference arm and into a sample arm, and superimposing light returning from the reference arm and from the sample arm; and detecting an intensity of interference of the superimposed light with a temporal resolution of a fraction of the output pulse width.

19. The method of claim 18, further comprising:
generating an external field acting on the medium, wherein the dispersion parameter of the medium is controlled or controllable by the external field.

20. The method of claim 18, further comprising:
sampling the intensity for a plurality of consecutive fractions corresponding to one output pulse width.

21. The method of claim 20, further comprising:
generating a series of input pulses at a repetition rate; and initiating the sampling at the repetition rate.

* * * * *